United States Patent
Wang et al.

(10) Patent No.: US 10,973,608 B2
(45) Date of Patent: Apr. 13, 2021

(54) DISPOSABLE PROTECTIVE ASSEMBLY APPARATUS FOR A DENTAL SYRINGE

(71) Applicant: Pac-Dent, Inc., Brea, CA (US)

(72) Inventors: Daniel Wang, Brea, CA (US); Taosheng Hu, Jiangsu (CN); Xiao Yang, La Habra, CA (US)

( * ) Notice: Subject to any disclaimer, the term of this patent is extended or adjusted under 35 U.S.C. 154(b) by 150 days.

(21) Appl. No.: 16/267,911

(22) Filed: Feb. 5, 2019

(65) Prior Publication Data
US 2019/0247145 A1    Aug. 15, 2019

Related U.S. Application Data

(60) Provisional application No. 62/628,868, filed on Feb. 9, 2018.

(51) Int. Cl.
*A61C 1/16* (2006.01)
*A61C 17/02* (2006.01)

(52) U.S. Cl.
CPC .............. *A61C 1/16* (2013.01); *A61C 17/02* (2013.01); *A61C 17/0202* (2013.01); *A61C 17/0217* (2013.01)

(58) Field of Classification Search
CPC ....... A61C 1/16; A61C 17/02; A61C 17/0202; A61C 17/0217
USPC ......................................................... 433/116
See application file for complete search history.

(56) References Cited

U.S. PATENT DOCUMENTS

| | | | | |
|---|---|---|---|---|
| 2,073,137 A | * | 3/1937 | Bimrose | A61C 1/16 433/116 |
| 4,723,912 A | * | 2/1988 | Nieusma | A61C 1/16 433/116 |
| 4,728,290 A | * | 3/1988 | Eisner | A61C 1/16 433/116 |
| 4,757,381 A | * | 7/1988 | Cooper | A61B 1/00091 206/369 |
| 4,810,194 A | | 3/1989 | Snedden | |
| 4,859,182 A | * | 8/1989 | Nerli | A61C 1/16 433/80 |
| 4,907,968 A | * | 3/1990 | Eisner | A61C 1/16 433/116 |
| 5,197,875 A | * | 3/1993 | Nerli | A61C 1/16 433/116 |
| 5,228,851 A | * | 7/1993 | Burton | A61C 1/16 206/306 |
| 5,267,860 A | * | 12/1993 | Ingram, Jr. | A61C 1/16 433/115 |
| 5,302,124 A | * | 4/1994 | Lansing | A61C 19/004 150/154 |
| 5,328,368 A | * | 7/1994 | Lansing | A61C 1/16 433/116 |
| 5,335,675 A | * | 8/1994 | Wheeler | B29C 65/222 128/842 |

(Continued)

FOREIGN PATENT DOCUMENTS

CA      2428624 A1    5/2002
WO      02/40082 A2   5/2002

*Primary Examiner* — Nicholas D Lucchesi

(57) ABSTRACT

Embodiments disclose a disposable protective assembly apparatus for a dental syringe body of a dental syringe. The apparatus is a combination of a disposable syringe tip and a disposable protective sleeve, the sleeve being pre-attached to the syringe tip, and the sleeve being in a pre-folded position to be quickly and easily slid over the dental syringe prior to a dental operation.

10 Claims, 6 Drawing Sheets

(56) References Cited

U.S. PATENT DOCUMENTS

| | | | | |
|---|---|---|---|---|
| 5,348,153 A | * | 9/1994 | Cole | A46B 5/04 15/167.1 |
| 5,407,354 A | * | 4/1995 | Fife | A61C 1/16 206/438 |
| 5,484,283 A | * | 1/1996 | Franetzki | A61B 1/042 433/116 |
| 5,487,201 A | * | 1/1996 | Hansen | A46B 5/04 132/309 |
| 5,542,845 A | * | 8/1996 | Jenkins | A61C 1/16 433/116 |
| 5,807,107 A | * | 9/1998 | Bright | A61C 19/004 433/116 |
| 5,921,776 A | | 7/1999 | Heilbrunn | |
| 8,752,579 B2 | * | 6/2014 | Bushman | A61C 17/08 137/527 |
| 9,433,468 B2 | * | 9/2016 | Wilt | A61B 50/00 |
| 2002/0103462 A1 | | 1/2002 | Nesbitt | |
| 2005/0181327 A1 | * | 8/2005 | Graham | A61C 1/16 433/116 |
| 2006/0111677 A1 | | 5/2006 | Nesbitt | |
| 2008/0213721 A1 | * | 9/2008 | Euvrard | A61C 3/03 433/116 |
| 2015/0100047 A1 | * | 4/2015 | Wilt | A61B 1/00144 606/1 |
| 2016/0184143 A1 | * | 6/2016 | Hooi | A61F 13/2082 604/286 |

\* cited by examiner

DISPOSABLE PROTECTIVE ASSEMBLY APPARATUS FOR A DENTAL SYRINGE

CROSS REFERENCE TO RELATED APPLICATIONS

This application claims priority under 35 U.S.C. § 119(e) to U.S. Provisional Application No. 62/628,868, filed Feb. 9, 2018, and entitled "Disposable Protective Assembly for Dental Syringe," the disclosure of which is hereby incorporated by reference in its entirety.

BACKGROUND OF THE INVENTION

1. Field of Invention

The present invention relates to a disposable protective assembly apparatus for effectively and efficiently protecting a dental air/water syringe during a dentistry operation, preventing cross-contamination between patients.

2. Description of Related Art

A dental air/water syringe is often used to dispense air and fluid to the inside of a patient's mouth during a dentistry operation. The dental syringe typically includes two components: a dental syringe body and an air/water syringe tip.

The dental syringe body is a conventional dentist tool known by those with skill in the art. The dental syringe body includes a handle for a dentist to hold on to, an electronic source of source of air and water, a hose, and valves or buttons for the dentist to press to deliver the air and water.

The syringe tip is a conventional dentist tool which attaches to the dental syringe body and passes air and water therethrough and into a dental patient's mouth. The syringe tip is typically a removable metal air/water syringe tip, where syringe tips are made to be removable for cleaning between uses.

The dental syringe body, unlike the syringe tip, is typically not changed or sterilized between uses, which can result in residual cross-contamination of the dental syringe body and transfer of contaminants from one dental patient to another.

Cross-contamination is the process by which bacteria or other microorganisms are unintentionally transferred from one substance or object to another, with harmful effect, even if the amount is small or residual. Residual cross-contamination between patients is of serious concern to the public and the dental profession. Without sufficient protection for the dental syringe body, contaminants can flow from a patient to the dental syringe body and to a future patient. This is because when the dental syringe dispenses air or water, the air or water may cause contaminants to pass from the patient to the dental syringe body, or vice versa. This problem has received considerable attention due to the publicity of many known illnesses and diseases which may be communicated by the transfer of contaminants between patients.

To combat cross contamination, disposable protective covers have been used in an attempt to protect dental syringes. Conventionally, there are mainly two types of protective covers—a protective cover with a syringe tip insertion opening and a protective cover without an opening.

The protective cover with a syringe tip insertion opening is the more popular of the two types with dental professionals. The opening passes the air water syringe tip therethrough. The opening usually has a dimension which is much larger than the dimension of the syringe tip, making this protective cover is easier to use. While this protective cover is structured for convenience, the opening leaves space for transmission of contaminants, bacteria, viruses, etc. to the dental syringe body that causes the problem of cross-contamination. As such, the protective cover with the syringe tip insertion opening unfortunately cannot effectively eliminate the risk of cross-contamination of the dental syringe body or a future patient.

The protective cover without an opening is a less popular choice with dental professionals. This protective cover requires a dental professional to poke a hole through the protective cover, with the end of the syringe tip. That creates a problem, as it becomes unavoidable to prevent the residue of the sleeve from getting into the dental syringe body and cause blockage after a certain number uses. In addition, a protective cover with a poked hole leaves space for potential contaminants to get into the dental syringe body.

While both types of protective covers try to prevent cross-contamination, neither are fully effective at preventing cross-contamination. A need remains for an effective, time-efficient, and well fit apparatus for protecting a dental air/water syringe during operation to prevent contamination of the dental syringe body and prevent transfer of such contaminants from one dental patient to another.

SUMMARY OF THE INVENTION

Embodiments disclose a disposable protective assembly apparatus for a dental syringe body of a dental syringe. The apparatus is a combination of a disposable syringe tip and a disposable protective sleeve, the sleeve being pre-attached to the syringe tip, and the sleeve being in a pre-folded position to be quickly and easily slid over the dental syringe prior to a dental operation.

An advantage of embodiments of the invention is the apparatus more effectively blocks contaminants. The pre-attached sleeve-tip forms an air tight seal that does not allow contaminants, including sleeve residue and residual cross contamination, to pass through to the dental syringe body or another patient.

Another advantage is the apparatus is quick to slip on and off, unlike conventional protective covers that are neither convenient to use nor time-efficient. The pre-attached sleeve-tip, along with the sleeve being in a pre-folded position, quickly and easily slides over the dental syringe body. The pre-attached sleeve is simply turned inside out to form an umbrella or canopy-like shape over the dental syringe body. The sleeve is initially in a pre-folded position is an easy-to-apply mechanism that allows dental professionals to unfold and apply it onto the syringe body in a time-efficient way, saving the dental professionals time and effort. This is unlike conventional protective covers, which required multiple complicated steps to be performed with precision, as a dental professional would have attached an air/water syringe tip from one container, and from another container, get a protective cover, aim the protective cover over the syringe body and tip being careful to avoid damaging the protective cover.

Another advantage is the apparatus has an improved fit. A sleeve that is not configured for a dental air/water syringe can be difficult or time consuming for a dental professional to apply and fit the sleeve onto the dental syringe body, and difficult to use the air/water control buttons. The sleeve has a size and shape structure configured especially for an air/water syringe, such that the sleeve is well fitted on an air/water dental syringe. The tip and the sleeve are tightly fit such that there is no opening on the sleeve that could possibly take in contaminants. By contrast, conventional protective covers are not structured specifically for dental air/water syringe and do not fit the dental syringe body well. The dental air/water syringe has a unique and special shape, such that a tight fitted cover is inconvenient to apply on to the dental syringe body, and a loose fitted cover makes it very difficult to use the dental syringe's air and water buttons. In order to make fitting not too challenging, often a conventional protective cover needs to be overly large with a large opening, making it difficult to use the buttons on the dental syringe body and increases cross contamination during usage of the air and water buttons.

A further advantage is an anti-slip texture on the sleeve in touch with the dental professional and the air water dental syringe. The anti-slip texture ensures the manipulation of the air and water controls. The anti-slip texture is on the exterior of the sleeve touching the dentist's hand that grips the syringe, and on the interior of the sleeve that touches the syringe body and buttons. This dual interior and exterior anti-slip texture allows the dentist to keep pressing the air button or the water button during operations. Dental operation requires accurate manual manipulation of controls, such that with an anti-slip structure, accurate manual manipulation of controls can be ensured and problems can be avoided. The anti-slip texture prevents the dental syringe from being slippery. Conventional protective covers do not have an anti-slip texture.

The foregoing, and other features and advantages of the invention, will be apparent from the following, more particular description of the preferred embodiments of the invention, the accompanying drawings, and the claims.

DETAILED DESCRIPTION OF THE INVENTION

The disposable protective assembly apparatus helps reduce cross-contamination between a dental syringe and dental patients. A syringe tip can readily engage with and disengage from a dental syringe body. A pre-attached sleeve-tip combination substantially and effectively prevents contaminants from being drawn through the syringe body. The pre-attached sleeve, along with the sleeve initially being in a pre-folded position, makes the apparatus is easy-to-use and time-efficient for dental professionals. The apparatus is removable and disposable after use with each patient, thereby minimizing the need to sterilize the dental syringe body after each use. The apparatus is specially structured for the shape of a dental air/water syringe and the apparatus has an anti-slip texture that is intended to maintain stable manipulation of controls during operation. Because the apparatus can be replaced without changing the dental syringe body, it significantly reduces the costs of dental procedures and prevents contamination of the dental syringe body.

Figure 1:
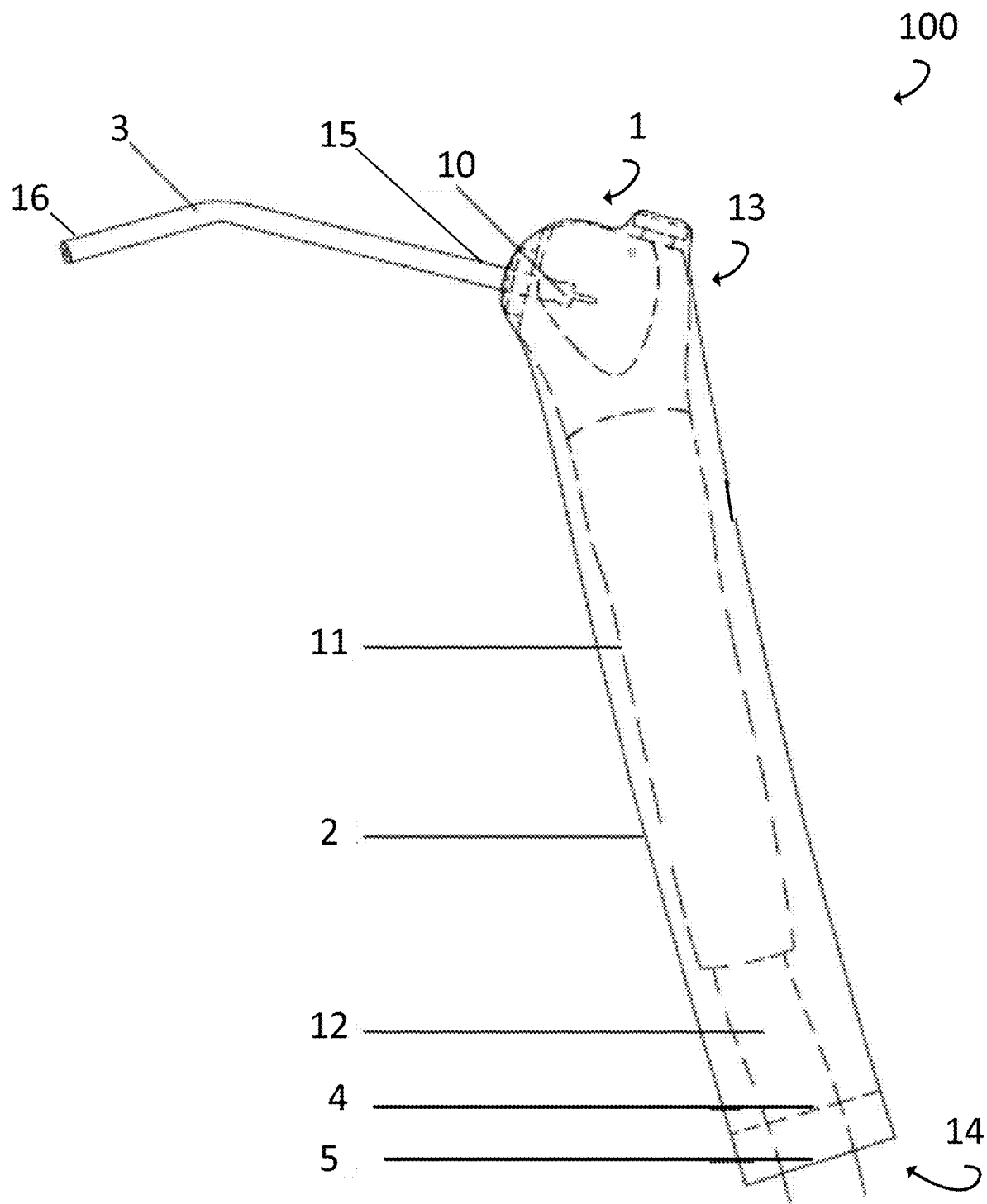
FIG. 1 illustrates a cut-away side view of a dental syringe system according to one embodiment of the invention.

FIG. 1 illustrates a cut-away side view of a dental syringe system 100 according to one embodiment of the invention. The system 100 quickly and effectively covers a dental air/water syringe 13. The system 100 includes a dental syringe body 11 and a disposable protective assembly apparatus 1, where the apparatus 1 includes a disposable protective sleeve 2 and a disposable air water syringe tip 3.

The syringe body 11 provides air and water to a dental patient, as is known in dentistry. The dental syringe body includes a retainer assembly configured to receive a syringe tip, air-water control buttons, and a utility hose 12. The utility hose 12 provides the air and water through the syringe body 11. The utility hose 12 includes two separate tubes inside, one for air and one for water. When a syringe tip is added to a dental syringe body, the device becomes a dental syringe, as is known in dentistry. The syringe body 11 receives the syringe tip 3 to form a dental syringe 13.

The disposable protective assembly apparatus 1 is an improved protective cover that covers the syringe body 11. The apparatus 1 is a combination of a sleeve 2 and tip 3 pre-attached or easily attached together, prior to the tip 3 being inserted into the syringe body 11. The apparatus 1 advantageously more effectively blocks contaminants from reaching the syringe body 11, quickly slips on and off, and improves access to the control buttons of the dental syringe body as the sleeve fits the dental syringe body well and the sleeve has an anti-slip structure.

The disposable sleeve 2, when used in combination with the syringe tip 3, provides a substantially protective covering for the syringe body 11. The sleeve 2 has an attached distal end 15, an open proximal end 14, a shorter wall 4, and a longer wall 5. The attached end 15 is attached near a proximal end 10 of the syringe tip 3. The open end 14 is configured to umbrella over the syringe body 11 such that the dental syringe 13 before operation. After operation, the open end 14 of the sleeve is slid off the syringe body 11. The shorter wall 4 is long enough to cover the entire syringe body 11. The longer wall 5 is configured to quickly unfold the sleeve to cover the syringe body 11 before operation and quickly remove the sleeve from the syringe body 11 after operation.

The disposable air/water syringe tip 3 has multiple channels that allow fluid and air to be dispensed from the syringe body. The syringe tip 3 has the attached proximal end 10 and a distal end 16. The proximal end 10 of the syringe tip 3 passes through the attached end 15 of the sleeve 2 and is configured to attach to the syringe body 11. The distal end 16 of the syringe tip 3 is located away from the syringe body 11. The syringe tip 3 is pre-attached to the sleeve 2 becoming an integral part of a distal end of the sleeve 2.

Figure 2:
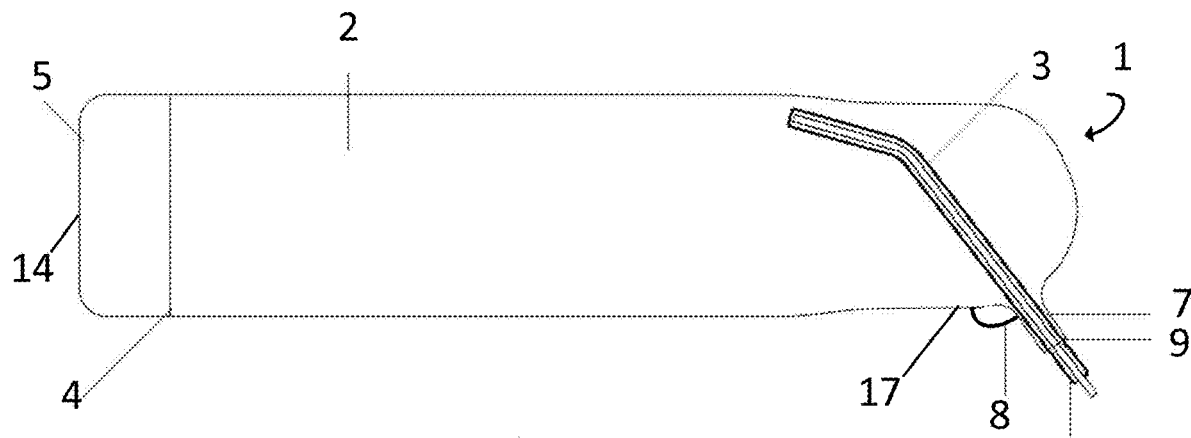
FIG. 2 illustrates a cut-away side view of a disposable protective assembly apparatus of the system with the sleeve not being folded according to one embodiment of the invention.

FIG. 2 illustrates a cut-away side view of the disposable protective assembly apparatus 1 of the system with the sleeve 2 not being folded according to one embodiment of the invention. The apparatus 1 is shown prior to attachment, without a syringe body. FIG. 2 illustrates components that will be difficult to see in FIG. 3 once the sleeve 2 is folded, as the folded sleeve partially blocks some components. FIG. 2 also introduces an extruded portion 7 of the sleeve 2, a predetermined non-zero angle 8, an outer surface 9 of the syringe tip 3, and a sleeve body 17.

The extruded portion 7 is located on the distal end of the sleeve 2. The extruded portion 7 connects the syringe tip 3 and the sleeve 2. The extruded portion 7 attaches onto an outer surface 9 of the proximal end 10 of the syringe tip 3. In one embodiment, the extruded portion 7 connects in a way that is not fixed but tight enough to avoid detachment of the syringe tip 3 and the sleeve 2 during operation, as well as prevent contaminants from getting into the syringe body 11. In another embodiment, the extruded portion is fixed to the syringe tip 3. The extruded portion 7 may make contact with the retainer assembly of the syringe body 11.

The predetermined non-zero angle 8 is the angle that the extruded portion 7 forms with the sleeve body 17 of the sleeve 2. The angle 8, in combination with the extruded portion 7, form an air sealed connected that does not allow contaminants through. The angle 8 tracks the proximal end 10 of the syringe tip 3 into syringe body 11 and ensures the convenience of unfolding the sleeve 2. In one embodiment, the angle 8 aligns with the angle of the retainer assembly of the dentist syringe body 11 when the dental syringe 13 is held upright. In another embodiment, the angle is about 135 degrees. The angle 8 of the sleeve's extruded portion is designed based on the angle between the syringe body 11 and the syringe tip 3 when attached. The angle 8 ensures the fit of the sleeve 2 to the syringe tip 3.

The outer surface 9 of the syringe tip 3 has a portion that is covered by the sleeve 2 prior to use, and a portion of the syringe tip 3 that is configured to insert into the dental syringe body 11.

The sleeve body 17 is the elongated portion of the sleeve and is configured to cover the length of the syringe body 11. The sleeve body 17, in combination with the extruded portion 7, forms the angle 8. The sleeve body 17 has a length when not folded that is greater than the longitudinal length of the syringe body 11 to cover the entire body of the dental syringe 13 and to cover a portion of the utility hose 12 connected to the dental syringe 13.

Figure 3:
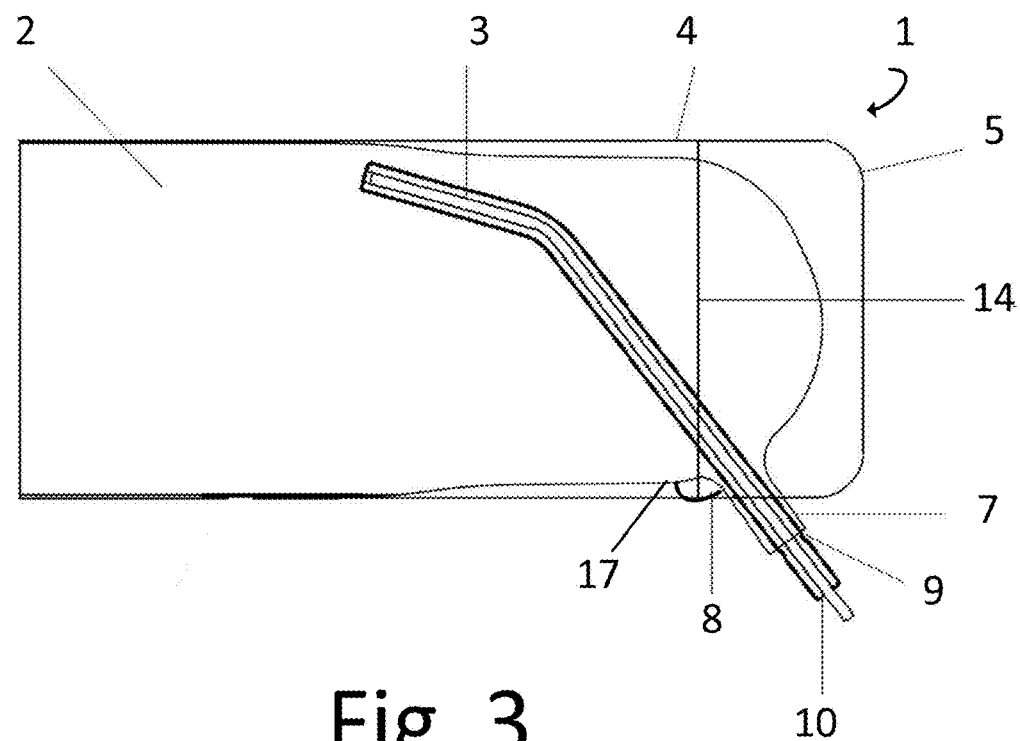
FIG. 3 illustrates a cut-away side view of the disposable protective assembly apparatus with the sleeve being folded according to one embodiment of the invention.

FIG. 3 illustrates a cut-away side view of the disposable protective assembly apparatus 1 with the sleeve 2 being folded according to one embodiment of the invention. This figure is identical to the previous figure except the sleeve 2 is in a pre-folded position. This figure also adds more detail to the apparatus 1, the sleeve 2, and the syringe tip 3.

The disposable protective assembly 1 is a sleeve-tip combination, with the sleeve 2 pre-attached to the syringe tip 3, in a pre-folded position as illustrated. The apparatus 1 is a disposable, time-efficient, and effective protective assembly for protecting dental syringe during operation and preventing contamination from being drawn back to the syringe body. The apparatus 1 is disposable and replaced after one use which greatly reduces the possibility of cross-contamination between dental patients. Although periodic sterilization of the dental syringe body may still be advisable for absolute safety, the need for sterilization is greatly reduced.

The sleeve 2 is pre-attached to the syringe tip 3. The sleeve 2 attaches to the outer surface 9 of the syringe tip 3 such that the syringe tip 3 does not need to poke through the sleeve 2 or leave an opening. In one embodiment, the syringe tip-sleeve attachment is permanent. In another embodiment, the syringe tip-sleeve attachment is tight enough to avoid detachment of the syringe tip and the sleeve during operation, but not permanently fixed. In this embodiment, the sleeve can being slidably attached to the syringe tip 3.

The sleeve 2 is made of a thin flexible material and may completely cover the entire syringe body 11 when unfolded backwardly. The extruded portion 7 of the sleeve 2 is connected to the proximal end 10 of the syringe tip 3.

The sleeve 2 is in a pre-folded position such that the open proximal end 14 of the sleeve 2 is folded towards the attached distal end 15 of the sleeve 2. In order to cover the syringe body 11 quickly, the pre-folded position does not cover the proximal end 10 of the syringe tip 3, such that the syringe tip 3 can directly connect into the syringe body 11. The pre-folded position starts to turn the sleeve 2 inside out. The pre-folded position has the sleeve 2 turned inside out at the open proximal end 14 of the sleeve 2, and the sleeve 2 is folded towards the attached distal end 15 of the sleeve 2. By pre-folding the sleeve 2 in this special structural way, it makes the apparatus 1 easier to use, in that the tip 3 directly inserts into the dental syringe body 11, and then the sleeve 2 easily unfolds to cover the dental syringe body 11.

The sleeve 2 has a plurality of walls including a shorter wall 4 and a longer wall 5. The shorter wall 4 has a length that is long enough to cover the entire syringe body 11. The shorter wall 4 is illustrated in the pre-folded position, such that the proximal open end 14 of the sleeve 2 is folded towards the proximal end 10 of the syringe tip 3. The longer wall 5 is configured to quickly unfold the sleeve to cover the syringe body 11 upon use. The longer wall 5 is also configured to quickly remove the sleeve 2 from the syringe body 11 after operation. The two walls 4, 5 each connect to each other on only one of their two sides, such that the walls 4, 5 together form the sleeve 2, a single layered sleeve. By having one wall 5 being longer than the other wall 4, this ensures the apparatus 1 quickly unfolds during the attachment and the removal.

The syringe tip 3 is configured to be push connected into the syringe body 11 such that the air and water buttons of the dental syringe 13 are ready to use. The syringe tip 3 is fully covered while the apparatus 1 is in the pre-folded position, prior to pulling the sleeve over the syringe tip 3 and syringe body 11.

Figure 4:
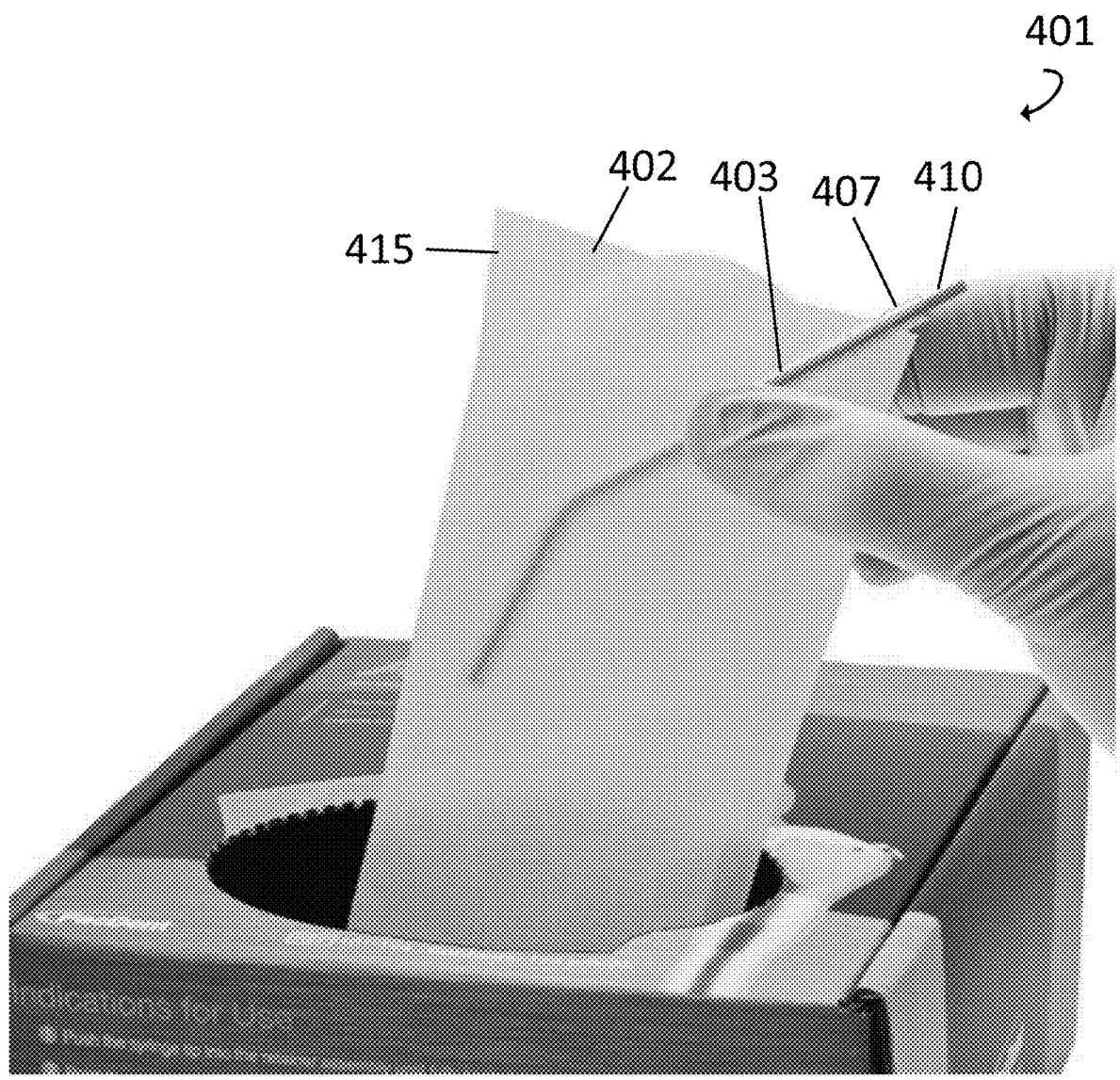
FIG. 4 illustrates a disposable protective assembly apparatus out of the box according to one embodiment of the invention.

FIG. 4 illustrates a disposable protective assembly apparatus 401 out of the box according to one embodiment of the invention. The apparatus 401 corresponds to apparatus 1 in the previous figures, and in some embodiments, is identical to the apparatus 1. Apparatus 401, like apparatus 1, provides the dental practitioner with a ready to use protective cover directly out of the box, and already in a pre-folded position. The apparatus 401 includes a disposable protective sleeve 402 and a disposable air water syringe tip 403.

The apparatus 401 has the disposable sleeve 402 that covers the entire body of the exterior surface of the dental air/water syringe body. The apparatus 401 also has the syringe tip 403 connected at the attached distal end 415 of the sleeve 402. The apparatus pre-folds the sleeve 402 in a way that allows the sleeve 402 to be quickly and effortlessly unfolded to cover the syringe body after the syringe tip 403 is attached to the syringe body. The apparatus 401 also has a tight connection between the sleeve 402 and the syringe tip 403, which leaves substantially no space for contaminants to get into the syringe body.

The disposable sleeve 402 ideally comprises a flexible, substantially transparent and sufficient thin material and is woven into an anti-slip texture that configured to accommodate manual manipulation of controls. The sleeve 402 is long enough to shield the entire body of the dental syringe and a portion of a utility hose connected to the dental syringe. The sleeve 402 comprises a special shape configured to fit the syringe body well when unfolded.

The sleeve 402 is formed of two parallel plane walls of different lengths, wherein a shorter wall has a length that is long enough to cover the entire syringe body, and a longer wall is configured to quickly unfold the sleeve to cover the syringe body upon use, and to quickly remove the sleeve from the syringe body after operation. The sleeve 402 is turned inside out and folded in a way that leaves a proximal end 410 of the syringe tip 403 out for easy attachment to a dental syringe body.

The sleeve 402 has an extruded portion 407 at an attached distal end 415 of the sleeve 402, and an opening on an open proximal end of the sleeve 402. The extruded portion 407 connects to an outer surface of the proximal end 410 of the syringe tip 403 to provide better protection against cross contamination. The sleeve 402, in this embodiment, is connected in a way that is not fixed but tight enough to avoid detachment of the syringe tip and the sleeve during operation. The sleeve 402 prevents contaminants from getting into the syringe body. The extruded portion 407 forms an angle that ensures the convenience of unfolding the sleeve 402.

The air water syringe tip 403 is pre-attached to the sleeve 402. During operation, the dental professional will simply attach the syringe tip 403 to a dental syringe body by inserting the proximal end 410 of the syringe tip 403 into the dental syringe body, and then unfolding the sleeve 402 by pulling a longer wall to cover the entire dental syringe body.

Figure 5:
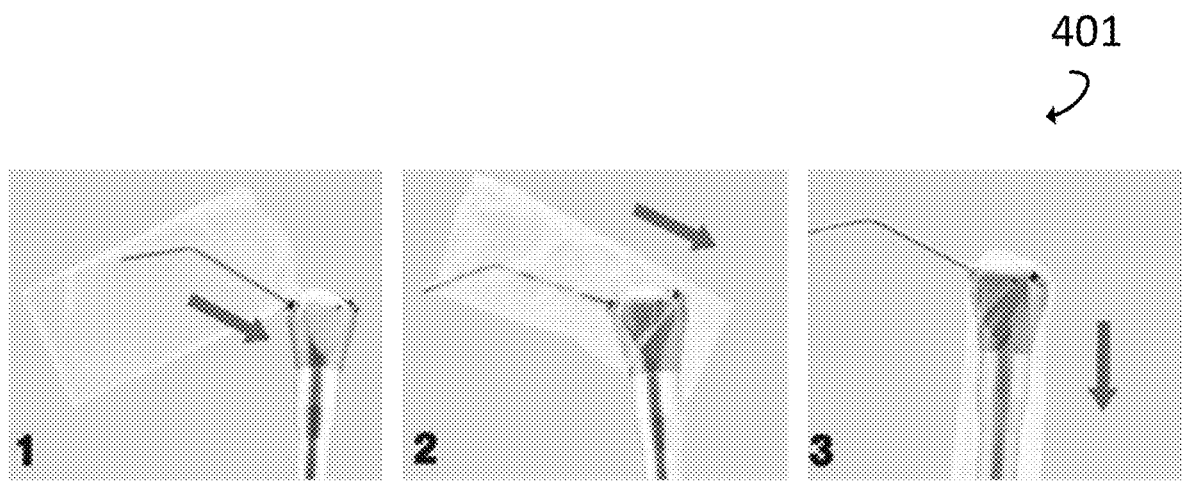
FIG. 5 illustrates the disposable protective assembly apparatus in three stages of attachment according to embodiments of the invention.

FIG. 5 illustrates the disposable protective assembly apparatus 401 in three stages of attachment according to embodiments of the invention. For attachment, in order to use the dental syringe, first the dental practitioner push connects the proximal end 410 of syringe tip 403 into a retainer assembly of the syringe body until the syringe tip 403 is fully seated, for example, until no groove of the syringe tip 403 is showing. Second, before use, the dental practitioner points the dental syringe at the floor and presses the air button several times to open the open proximal end of the sleeve 402, then turns the sleeve 402 inside out, starting to cover the syringe body. Lastly, the dental practitioner pulls the sleeve 402 across the syringe tip 403 and down the syringe body until the sleeve fully covers the entire dental syringe. The attached distal end 415 of the sleeve 402 stays near the proximal end 410 of the syringe tip 403, such that the sleeve 402 is covers the entire syringe body, and almost none of the tip 403. The dental syringe body is fully protected from cross contamination.

Figure 6:
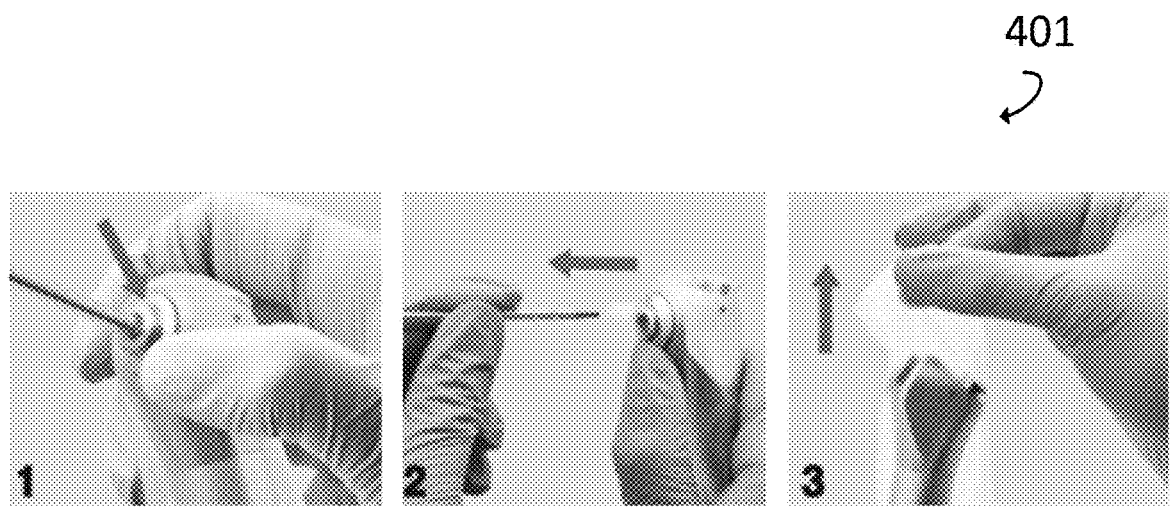
FIG. 6 illustrates the disposable protective assembly apparatus in three stages of removal according to embodiments of the invention.

FIG. 6 illustrates the disposable protective assembly apparatus 401 in three stages of removal according to embodiments of the invention. For removal, the dental practitioner first presses down the locking/unlocking mechanism on the retainer assembly of the dental syringe body, where the mechanism unlocks the syringe tip 403 for removal. Second, the dental practitioner pulls the syringe tip 403 straight of the syringe body, where the sleeve 402 is broken from the action of the dental practitioner pulling the tip 402 out from the syringe body. Lastly, the dental practitioner easily pulls the sleeve 2 up and over the shaft of the syringe body 11, removing the sleeve 2 that has been broken open from the action of the dental practitioner pulling the tip 402 out from the syringe body.

Figure 7:
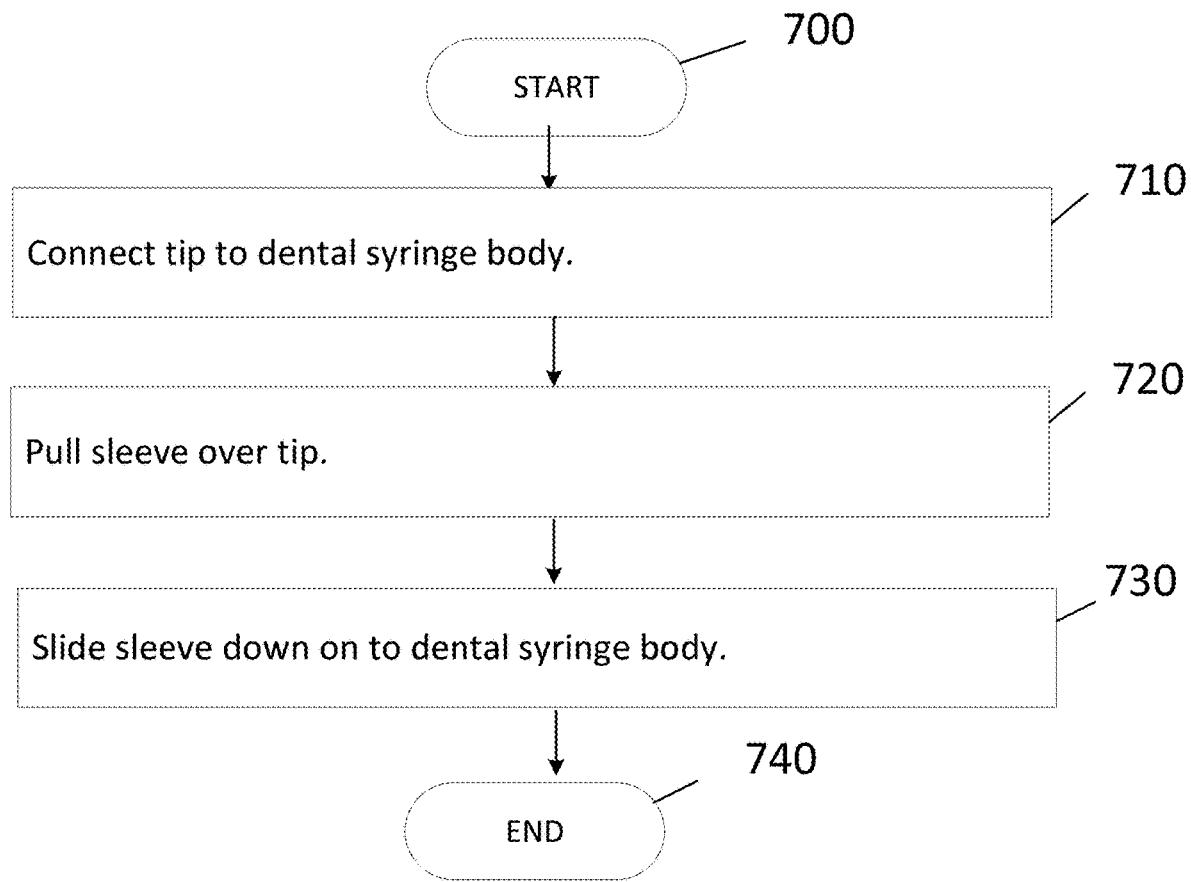
FIG. 7 illustrates a flow chart for attaching the disposable protective assembly apparatus to a dental syringe body according to embodiments of the invention.

FIG. 7 illustrates a flow chart for attaching the disposable protective assembly apparatus 1 or 401 to the dental syringe body 11 according to embodiments of the invention. The process starts at step 700. At step 710, the dental practitioner connects the proximal end 10 of the syringe tip 3 to the syringe body 11 by pushing in the syringe tip 3. At step 720, the dental practitioner pulls or unfolds the sleeve 2 over the syringe tip 3 and onto the syringe body 11. At step 730, the dental practitioner slides the sleeve 2 down the dental syringe body 11 to fully cover the dental syringe 13. The process ends at step 740.

Figure 8:
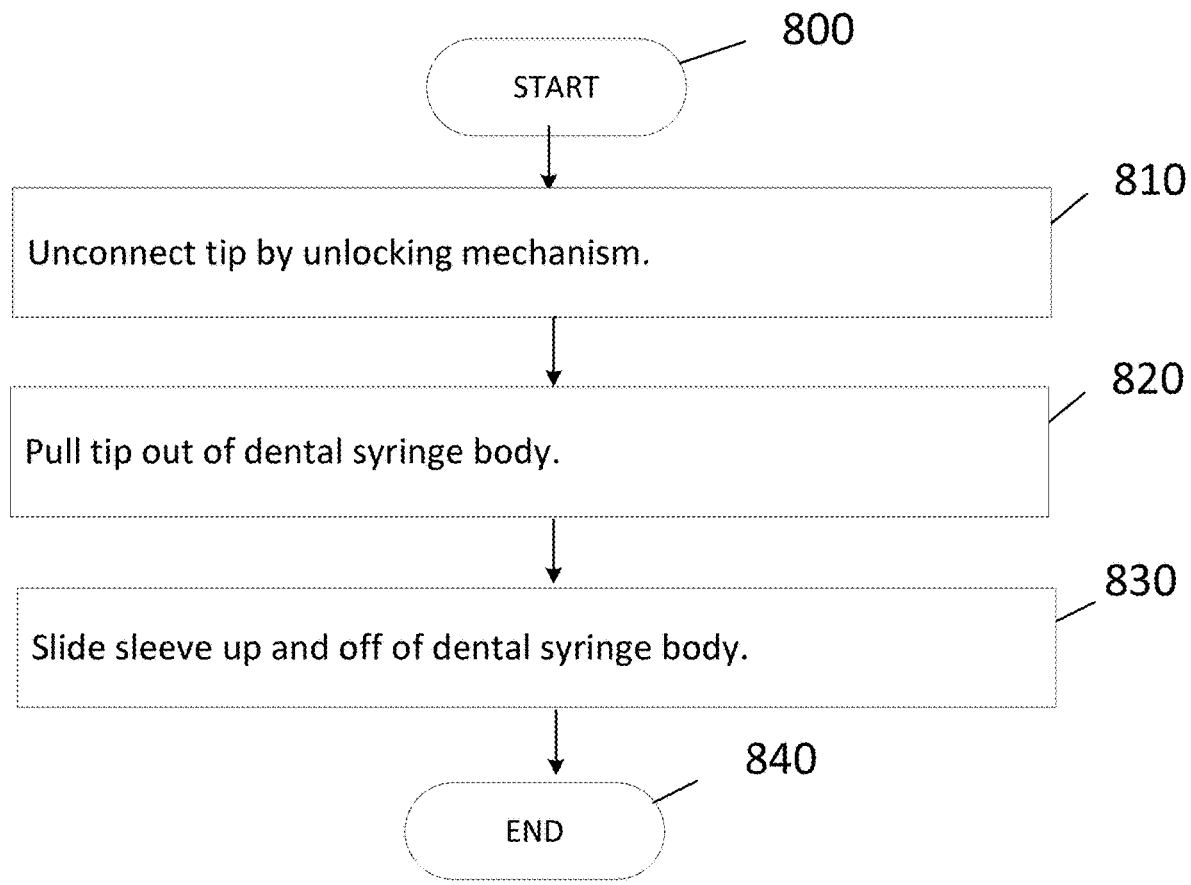
FIG. 8 illustrates a flow chart for removing the disposable protective assembly apparatus from the dental syringe body according to embodiments of the invention.

FIG. 8 illustrates a flow chart for removing the disposable protective assembly apparatus 1 or 401 from the syringe body 11 according to embodiments of the invention. The process starts at step 800. At step 810, the dental practitioner pushes the unlocking mechanism to remove the syringe tip 3. At step 820, the dental practitioner pulls or removes the syringe tip 3 from the syringe body 11. At step 830, the dental practitioner pulls or slides the sleeve 2 up and off the dental syringe body, removing the sleeve from the dental syringe 13. The process ends at step 840.

Further, the disclosure comprises embodiments according to the following clauses:

Clause 1: A protective assembly comprising: a disposable tip configured to be attached to a dental syringe body; a folded disposable sleeve formed of two parallel plane walls with an opening on the proximal end, configured to cover a syringe body during operation; and an extruded portion on the distal end of the sleeve being attached onto the outer surface of the proximal end of the syringe tip to connect the syringe tip and the sleeve.

Clause 2: The assembly in Clause 1, wherein the sleeve is turned inside out and folded in a way that leaves the proximal end of the syringe tip out for easy attachment to a dental syringe body.

Clause 3: The assembly in Clause 1, wherein the sleeve is folded in a unique way that could be easily unfolded to cover the dental syringe when the syringe tip is attached on the syringe body.

Clause 4: The assembly in Clause 1, wherein the folded sleeve is attached onto the outer surface of the proximal end of the syringe tip in an angle that ensures the convenience of unfolding the sleeve.

Clause 5: The assembly in Clause 1, wherein the sleeve, when unfolded, has a length which is greater than the longitudinal length of a dental syringe to cover the entire body of the dental syringe and to cover a portion of a utility hose connected to the dental syringe.

Clause 6: The assembly in Clause 1, wherein the sleeve, when unfolded, comprises a special shape configured to fit the air/water syringe body well.

Clause 7: The assembly in clause 1, wherein the two parallel plane walls of the sleeve are of different lengths, wherein the longer one is configured to quickly unfold the sleeve to cover the syringe body upon use, and to quickly remove the sleeve from the syringe body after operation.

Clause 8: The assembly in clause 1, wherein the extruded portion on the sleeve is attached onto the outer surface of the proximal end of the syringe tip, in a way that is not fixed but tight enough to avoid detachment of the syringe tip and the sleeve during operation.

Clause 9: The assembly in Clause 1, wherein the sleeve comprises a flexible, substantially transparent and sufficient thin material configured to accommodate manual manipulation of controls.

Clause 10: The assembly in Clause 1, wherein the sleeve is woven into an anti-slip texture that is intended to maintain stable manipulation of controls during operation.

Clause 11: A method comprising: attaching a disposable protective assembly to a dental syringe body by inserting the distal end of a syringe tip into the syringe body; and unfolding a pre-folded sleeve formed of two parallel plane walls to cover the entire syringe body.

Clause 12: The method in Clause 11, wherein the sleeve is turned inside out and folded in a way that leaves the proximal end of the syringe tip out for easy attachment to a dental syringe body.

Clause 13: The method in Clause 11, wherein the sleeve is folded in a unique way that could be easily unfolded to cover the dental syringe when the syringe tip is attached onto the syringe body.

Clause 14: The method in Clause 11, wherein the folded sleeve is attached onto the outer surface of the outer surface of the proximal end of the syringe tip in an angle that ensures the convenience of unfolding the sleeve.

Clause 15: The method in Clause 11, wherein the sleeve, when unfolded, has a length which is greater than the longitudinal length of a dental syringe to shield the entire body of the dental syringe and to shield a portion of a utility hose connected to the dental syringe.

Clause 16: The method in Clause 11, wherein the sleeve, when unfolded, comprises a special shape configured to fit the air/water syringe body well.

Clause 17: The method in Clause 11, wherein the two parallel plane walls of the sleeve are of different length, wherein the longer one is configured to quickly unfold the sleeve to cover the syringe body upon use, and to quickly remove the sleeve from the syringe body after operation.

Clause 18: The method in Clause 11, wherein the sleeve comprises an extruded portion on the distal end to be attached onto the outer surface of the proximal end of the syringe tip, in a way that is not fixed but tight enough to avoid detachment of the syringe tip and the sleeve during operation.

Clause 19: The method in Clause 11, wherein the sleeve comprises a flexible, substantially transparent and sufficient thin material configured to accommodate manual manipulation of controls.

Clause 20: The assembly in Clause 11, wherein the sleeve is woven into an anti-slip texture that is intended to maintain stable manipulation of controls during operation.

Further features and advantages of the invention, as well as the structure and operation of various embodiments of the invention, are described in detail with reference to the accompanying FIGS. 1-8, wherein like reference numerals refer to like elements. Although the illustrations illustrate the sleeve attached at a particular portion of the syringe tip, one with skill in the art could attach the sleeve at another portion without departing from the spirit of the invention.

It is to be recognized that depending on the embodiment, certain acts or events of any of the methods described herein can be performed in a different sequence, may be added, merged, or left out altogether (for example, not all described acts or events are necessary for the practice of the method). Moreover, in certain embodiments, acts or events may be performed concurrently, for example, through multi-threaded processing, interrupt processing, or multiple processors, rather than sequentially.

It is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

It should be understood that the invention is not limited to the embodiments set forth herein for purposes of exemplification, but is to be defined only by a fair reading of the appended claims, including the full range of equivalency to which each element thereof is entitled. Although the invention has been described with reference to the above examples, it will be understood that modifications and variations are encompassed within the spirit and scope of the invention. Accordingly, the invention is limited only by the following claims.

What is claimed is:

1. A disposable protective assembly apparatus for a dental syringe body, the apparatus comprising:
a syringe tip configured to connect to the dental syringe body of a dental syringe, wherein the syringe tip is disposable; and
a sleeve attached to the syringe tip, wherein the sleeve is disposable and in a pre-folded position, the sleeve having an open end and an attached end, wherein the attached end of the sleeve is attached to the syringe tip and the open end of the sleeve is configured to slide onto the dental syringe body to cover the dental syringe body during operation and the open end of the sleeve is configured to slide off of the dental syringe body after operation;
wherein the sleeve in the pre-folded position has the open end of the sleeve folded towards the attached end of the sleeve.

2. A disposable protective assembly apparatus for a dental syringe body, the apparatus comprising:
a syringe tip configured to connect to the dental syringe body of a dental syringe, wherein the syringe tip is disposable; and
a sleeve attached to the syringe tip, wherein the sleeve is disposable and in a pre-folded position, the sleeve having an open end and an attached end, wherein the attached end of the sleeve is attached to the syringe tip and the open end of the sleeve is configured to slide onto the dental syringe body to cover the dental syringe body during operation and the open end of the sleeve is configured to slide off of the dental syringe body after operation;
wherein the pre-folded position does not cover a proximal end of the syringe tip, wherein the proximal end of tip is configured to connect directly into the dental syringe body.

3. A disposable protective assembly apparatus for a dental syringe body, the apparatus comprising:
a syringe tip configured to connect to the dental syringe body of a dental syringe, wherein the syringe tip is disposable; and
a sleeve attached to the syringe tip, wherein the sleeve is disposable and in a pre-folded position, the sleeve having an open end and an attached end, wherein the attached end of the sleeve is attached to the syringe tip and the open end of the sleeve is configured to slide onto the dental syringe body to cover the dental syringe body during operation and the open end of the sleeve is configured to slide off of the dental syringe body after operation;

wherein the pre-folded position is turned inside out.

4. A disposable protective assembly apparatus for a dental syringe body, the apparatus comprising:
- a syringe tip configured to connect to the dental syringe body of a dental syringe, wherein the syringe tip is disposable; and
- a sleeve attached to the syringe tip, wherein the sleeve is disposable and in a pre-folded position, the sleeve having an open end and an attached end, wherein the attached end of the sleeve is attached to the syringe tip and the open end of the sleeve is configured to slide onto the dental syringe body to cover the dental syringe body during operation and the open end of the sleeve is configured to slide off of the dental syringe body after operation;
- wherein the sleeve comprises an extruded portion configured to align with a proximal end of the syringe tip.

5. The apparatus of claim 4, wherein the extruded portion of the sleeve forms a non-zero predetermined angle with a sleeve body.

6. The apparatus of claim 4, wherein the extruded portion of the sleeve attaches to an outer surface of the syringe tip.

7. A dental syringe system, the system comprising:
- a dental syringe with a dental syringe body;
- a syringe tip configured to connect to the dental syringe body of the dental syringe, wherein the syringe tip is disposable; and
- a sleeve attached to the syringe tip, wherein the sleeve is disposable and in a pre-folded position, the sleeve having an open end and an attached end, wherein the attached end of the sleeve is attached to the syringe tip and the open end of the sleeve is configured to slide onto the dental syringe body to cover the dental syringe body during operation and the open end of the sleeve is configured to slide off of the dental syringe body after operation;
- wherein the sleeve in the pre-folded position has the open end of the sleeve folded towards the attached end of the sleeve.

8. The system of claim 7 further comprising a utility hose, the utility hose providing air and water through the dental syringe body and the syringe tip.

9. A method of protecting a dental syringe body, the method comprising:
- connecting a syringe tip to the dental syringe body of a dental syringe, wherein the syringe tip is disposable; and
- sliding a sleeve down the dental syringe body, the sleeve attached to the syringe tip, wherein the sleeve is disposable and in a pre-folded position, the sleeve having an open end and an attached end, wherein the attached end of the sleeve is attached to the syringe tip and the open end of the sleeve is configured to slide onto the dental syringe body to cover the dental syringe body during operation and the open end of the sleeve is configured to slide off of the dental syringe body after operation;
- wherein the sleeve in the pre-folded position has the open end of the sleeve folded towards the attached end of the sleeve.

10. A method of protecting a dental syringe body, the method comprising:
- connecting a syringe tip to the dental syringe body of a dental syringe, wherein the syringe tip is disposable; and
- sliding a sleeve down the dental syringe body, the sleeve attached to the syringe tip, wherein the sleeve is disposable and in a pre-folded position, the sleeve having an open end and an attached end, wherein the attached end of the sleeve is attached to the syringe tip and the open end of the sleeve is configured to slide onto the dental syringe body to cover the dental syringe body during operation and the open end of the sleeve is configured to slide off of the dental syringe body after operation;
- further comprising unfolding the sleeve from the pre-folded position to pull the sleeve down the dental syringe body.

* * * * *